G. ERMOLD.
SURGICAL INSTRUMENT.
APPLICATION FILED MAY 27, 1919.
Reissued Mar. 22, 1921.
15,071.
2 SHEETS—SHEET 1.
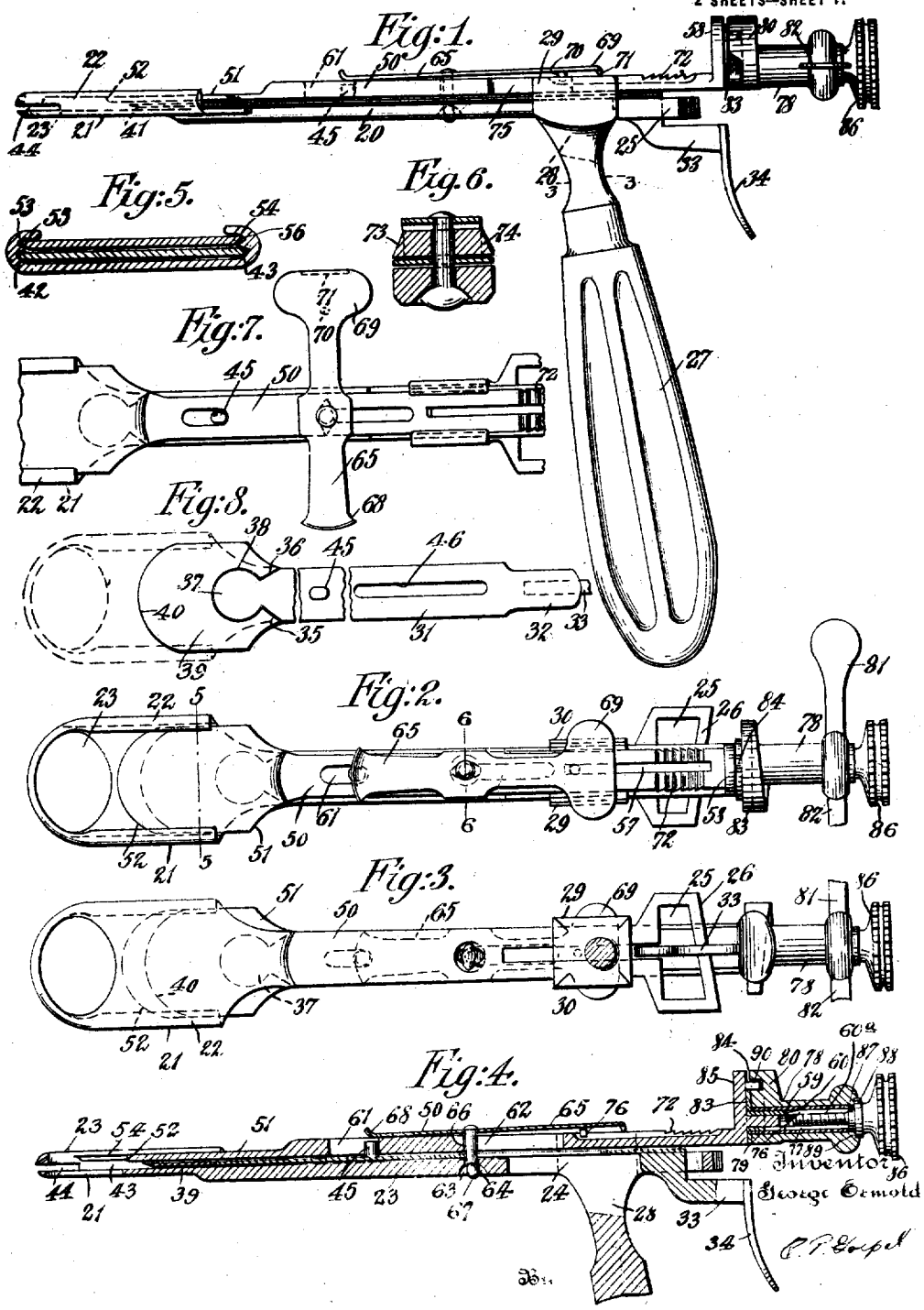

G. ERMOLD.

SURGICAL INSTRUMENT.

APPLICATION FILED MAY 27, 1919.

Reissued Mar. 22, 1921. 15,071.

2 SHEETS—SHEET 2.

Inventor

George Ermold

By C. P. Goepel

Attorney

UNITED STATES PATENT OFFICE.

GEORGE ERMOLD, OF NEW YORK, N. Y.

SURGICAL INSTRUMENT.

15,071. Specification of Reissued Letters Patent. Reissued Mar. 22, 1921.

Original No. 1,299,228, dated April 8, 1919, Serial No. 204,341, filed November 28, 1917. Application for reissue filed May 27, 1919. Serial No. 300,235.

*To all whom it may concern:*

Be it known that I, GEORGE ERMOLD, a citizen of the United States, and resident of the borough of Manhattan, in the county, city, and State of New York, have invented certain new and useful Improvements in Surgical Instruments, of which the following is a specification.

The present invention relates to improvements in surgical instruments, and particularly to such instruments known in the profession as surgical snares, and used principally for the removal of tonsils. One object of the present embodiment of my invention, is the production of such an instrument having two distinct actions, namely, a preliminary crushing action and a secondary cutting action, both of which may be accurately and conveniently controlled by the same hand holding the instrument.

A further object is to provide a very powerful crushing action with very little exertion on the part of the surgeon, and without danger of so shaking or moving the instrument as to injure the patient. It is also proposed to automatically bring the cutting member into a position preliminary to the cutting action, after which the cutting member may be manually operated independently of the crusher.

A still further object is to provide a crusher, which will at the same time securely provide and securely hold and retain the severed member and to provide at the same time a perfect cutting action in connection therewith, to the end that the operation may be carried on in a convenient, safe, and scientific manner.

It is also proposed to provide an instrument free from projections, and of such shape and dimensions that the same may be placed in the patient's mouth without causing a great deal of discomfort, and which will at the same time permit the surgeon to operate in an efficient manner.

Further objects are simplicity of construction, possibility of convenient disassembling of the parts for cleaning purposes, and the provision of a detachable cutting member which may be readily renewed, or sharpened.

With these and other objects in view, an embodiment of my invention is shown, by way of example, in the accompanying drawings, and this embodiment will be hereinafter more fully described with reference thereto, and the invention will be finally pointed out in the claims.

In the accompanying drawings:

Figure 1 is a side elevation of an instrument embodying my invention;

Fig. 2 is a top plan view thereof;

Fig. 3 is a bottom plan view of the same, the handle being broken away;

Fig. 4 is a longitudinal vertical sectional view;

Fig. 5 is a transverse sectional view along the line 5—5 of Fig. 2;

Fig. 6 is a transverse sectional view along the line 6—6 of Fig. 2;

Fig. 7 is a fragmentary plan view showing the retaining member turned into position to permit disassembling of the parts;

Fig. 8 is a plan view with parts broken away, of the cutting member and the slide plate for operating the same;

Similar reference characters indicate corresponding parts throughout the several figures of the drawings.

Figure 9:
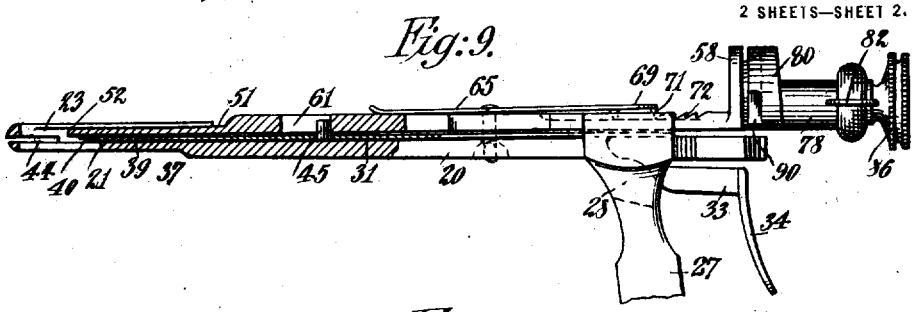
Figs. 9, 10 and 11 are views partly in section and partly in elevation, showing respectively the initial operated position of the parts, the second position in which the crushing member has been fully operated, and the cutting member brought into its position preliminary to cutting, and the final position in which the cutting member has been fully operated.

Referring to the drawings, and more particularly to Fig. 1 thereof, the present embodiment of my improved device comprises a longitudinal supporting base 20, preferably flat at its upper side, and rounded at its under side, provided at its forward end with a laterally disposed guide head or nose 21, having an upstanding rim portion 22 extending about the sides and front end thereof, and provided with an elliptical aperture 23 adjacent the forward end. The rear end of the base 20 is slotted as at 24, and terminates in an enlarged open portion 25 communicating with the slot, and having its rear wall 26 obliquely disposed, the shape of the opening in the present embodiment being substantially trapezoidal.

A depending handle 27, forked at its upper end as at 28, embraces the base portion 20 in front of and adjacent the enlarged open portion 25, and extends slightly above the base portion, providing flanges 29 and 30 extending slightly over the base, and having their inner faces beveled. The open portion of the forked end of the handle extends downwardly from, and communicates with the slot 24 of the base.

A knife operating slide plate 31 is disposed at the upper side of the base 20, and is provided at its rear end with a reduced portion 32, to the underside of which is secured a neck 33 provided at its outer end with a thumb piece 34. At the forward end the slide 31 is cut inwardly as at 35 and 36 to a circular head portion 37, which is adapted to interlockingly engage a correspondingly shaped cut-out portion 38 of the knife or cutting member 39.

The cutting member 39 is provided with an arcuate cutting edge 40, beveled at its under side as at 41, and the longitudinal edges of the said member engage guide slots 42 and 43 provided in the rim 22 of the head 21. The forward end of the head 21 substantially conforms in shape to the cutting edge 40, and is provided with a slot 44 into which the cutting edge is adapted to be moved.

A pin or lug 45 is provided at the upper side of the slide plate 31, and rearwardly of the same there is provided a longitudinal slot 46 adapted to permit movement of the slide plate with respect to the shank of a retaining member, which will be presently more fully described. When the slide plate 31 is moved forwardly to the position indicated in Fig. 11, the reduced end 32 thereof, providing the other parts of the instrument are detached, will permit of the slide plate being lifted from the base, the thumb piece 34 being free to move through the open portion 25, and the reduced portion 32 permitting the passage of the slide plate between the flanges 29 and 30.

At the upper side of the slide plate 31 there is provided a reciprocating crusher bar 50, provided at its forward end with a laterally disposed crusher head 51, having an arcuate edge 52, somewhat blunt, and having its longitudinal side edges 53 and 54 beveled at their under sides, and disposed in guide slots 55 and 56 of the rim 22. The crusher head 51 is slightly less in width than the cutting member 39, so that it is impossible to accidentally place the cutting member in the slots 55 of the crusher head, the distance between these slots, it will be understood, being also less than the width of the cutting member. The arcuate edge 52 substantially conforms to the interior of the arcuate forward end of the rim 22, and coöperates therewith to produce a crushing effect, and also provides a gripping or retaining means to hold the tonsil, or the like, before and after the severing thereof.

The rearward portion of the crusher bar 50 is longitudinally channeled as at 57, and at the end of the said bar there is provided an upstanding support 58.

A slot 61 is provided rearwardly of the crusher head, and engages the lug or pin 45 of the slide plate 31, and between this slot 61 and the channel 57, there is provided a longitudinal slot 62 which registers with the slot 46 of the slide plate 31, and also with an I-shaped opening 63 in the base 20, the said opening being surrounded at the under side of the base 20 by a substantially circular recess 64. A spring retaining member 65 is provided with a shank 66, having a knob 67 at the end thereof adapted to be passed through the slots 62 and 46, and also the opening 63 in the base, when the said member is turned at right angles to the base as indicated in Fig. 7. When turned into alinement with the said base, it is adapted to lock the parts together. The slots 62 and 46 permit sliding movement of the respective crusher bar and slide plate with respect to the base 20, while the slot 61 permits further sliding movement of the slide plate with respect to the crusher bar. To this end, the combined lengths of the slots 62 and 61 are substantially equal to the length of the slot 46.

The spring retaining member 65 is curved upwardly at its forward end as at 68, and at its rearward end is provided with an enlarged portion 69, having a lug 70 at the under side thereof, which engages the channel 57, and provided at its rear edge with a depending tooth 71, adapted to engage the ratchet teeth 72 cut in the crusher bar, and disposed at each side of the said channel 57. These teeth are inclined rearwardly so that the tooth 71, by reason of the resiliency of the retaining member, permits forward movement of the crusher bar with respect thereto, but locks the same against rearward movement.

The enlarged portion 69 of the retaining member extends slightly beyond the longitudinal edges of the crusher bar, which permits of the same being readily gripped by the thumb and forefinger, and lifted to disengage the lug 70 from the channel 57 to permit of the said retaining member being turned into the disengaging position shown in Fig. 7.

The side edges of the crusher bar are beveled as at 73 and 74 so that the same will interlockingly engage the beveled inner faces of the flanges 29 and 30. At one portion of the said edges there are provided straight cut portions 75 of a length slightly greater than the length of the flanges 29 and 30, and which permit of the disengagement of the crusher bar when the said straight cut portions are brought into relation with the said flanges.

Figure 13:
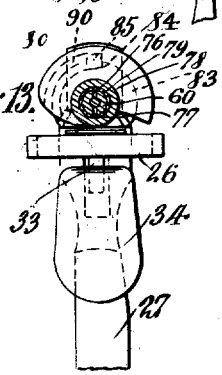
Fig. 13 is a vertical sectional view taken along the line 13—13 of Fig. 12.
Figure 15:
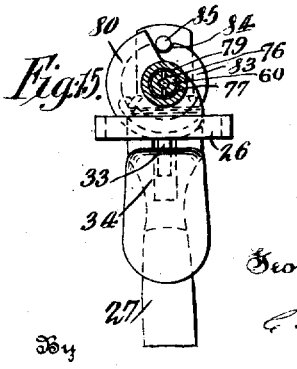
Fig. 15 is a vertical sectional view taken along the line 15—15 of Fig. 14.

The upstanding support 58 is provided with a stud 59 upon which there is secured a tubular shaft or spindle 60. The shaft 60 (see Figs. 4 and 13), is split from the outer end for the greater part of its length as at 76 and 77, forming thereby a spring shaft upon which there is rotatably mounted a crusher handle comprising a sleeve 78 provided interiorly with a spring lining 79 secured to the sleeve, and adapted to be slightly expanded outwardly, and which cooperates with the spring shaft 60 to securely retain the wedge handle in any desired position. At the forward portion of the sleeve 78 there is provided a spiral cam portion 80, and at its rear end there are provided wing shaped handle portions 81 and 82. A flat spring 83 is provided on the shaft 60 between the support 58 and the cam portion 80, and is prevented from rotation by engagement of a recess 84 therein, with a pin 85 provided on the upstanding support 58.

A retaining thumb screw 86 is secured in the screw threaded bore 60[a] of the shaft 60, a shoulder 87 thereof engaging the end of the said shaft, while a second shoulder 88 loosely engages an annular recess 89 provided in the end of the wedge handle, so that while the thumb screw is tightly secured to the shaft 60, the wedge handle is not prevented from rotation, the flat spring 83 holding the wedge handle always in resilient engagement with the flange 89. The engagement of the screw 86 with the shaft 60 causes the same to expand slightly against the spring lining 79, thereby forming a resilient hold for the wedge handle.

An arcuate slot 90 is provided on the inner face of the spiral cam portion 80, extending from the enlarged end of the said member to a point intermediate the enlarged and the small end of the same, and cooperates with the pin 85 to limit the movement in one direction of the wedge handle, the engagement of the pin with the small end of the cam portion 80 limiting the movement in the other direction.

Figure 12:
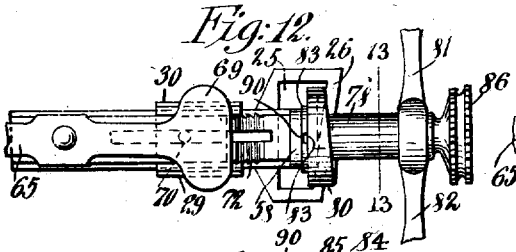
Fig. 12 is a plan view with parts broken away, showing the mechanism for operating the crushing member in its position just prior to operation.

The action afforded by the wedge handle is especially intended for use where a very powerful crushing effect is desired, the crusher bar first being brought to the position indicated in Fig. 12, which is the position preliminary to the crushing, so that the cam portion is in operative relation with the enlarged portion 25, the spiral surface of the cam coöperating with the oblique wall 26, upon turning of the wedge handle, to slowly move the crusher bar forwardly with a very powerful crushing action.

The operation of my improved instrument is as follows: Fig. 1 represents the parts prior to the forward movement of either the crusher bar or cutting member. I will first describe the operation of the instrument without bringing into play the wedge handle.

Referring to Figs. 1, 9, 10 and 11, the instrument is first placed in the throat of the patient, with the parts in the position indicated in Fig. 1, in which the elliptical aperture 23 is fully open. By means of the thumb engaging the thumb screw 86, the crusher bar is moved forwardly to the position indicated in Fig. 9. During this movement, it will be noted, the slot 61 causes the crusher bar to also move the slide plate 31 and the cutting member forwardly.

Figure 10:
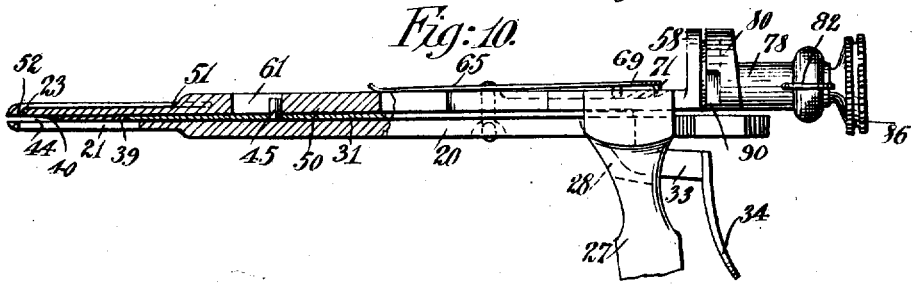

From the position indicated in Fig. 9, the crusher bar is forced forwardly to the position indicated in Fig. 10, the ratchet teeth during this action preventing any backward movement of the crusher bar, so that a powerful crushing action results, and by cooperation of the blunt edge 52 of the crusher head with the closed forward end of the nose of the head 21, a gripping action results. As above pointed out, the knife or cutting member has been moved forwardly during this action, and is brought to the position indicated in Fig. 10, preliminary to cutting.

Figure 11:
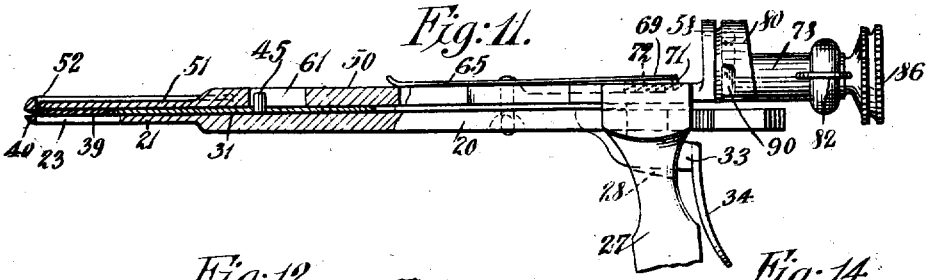

The thumb is now engaged with the thumb piece 34, and the knife or cutting member is forced forwardly, the cutting edge entering the slot 44 and completing the operation, as indicated in Fig. 11. In order to move the parts back to their original positions, the thumb and forefinger are engaged beneath the enlarged projecting portions of the spring retaining member 65, and the tooth 71 is lifted out of engagement with the ratchet teeth 72. By pulling with the other hand the parts may be retracted. The pin 70 is slightly longer than the tooth 71, so that during this action, the same is not disengaged from the channel 57.

In order to disassemble the parts, the spring retaining member is lifted to such extent that the pin 70 is disengaged from the channel 57, and thereupon the retaining member may be turned to the position indicated in Fig. 7, permitting disengagement of the retaining member, and a consequent release of the crusher bar and slide plate. This convenient disassembling and assembling of the instrument is quite important, in that it greatly simplifies the sterilizing process, and permits of the renewal of the cutting member with facility.

Figure 14:
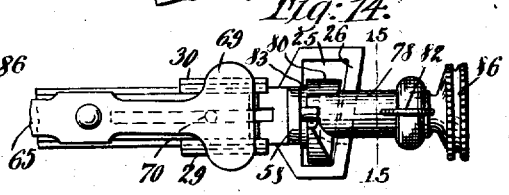
Fig. 14 is a view similar to Fig. 12, showing the mechanism in its operated position.

In Figs. 12 to 15, I have illustrated the action of the wedge handle, Fig. 12 showing the position of the parts preliminary to the wedge action, and Fig. 14 showing the final position. The pin 85 prevents further movement of the spiral cam when the crusher bar is moved to its full forward position, so that any further movement which might break the end of the head or nose 21, is prevented.

With the present embodiment of my invention, it will be seen, an instrument is provided in which there is a preliminary crushing action and a final wedge, and crushing effect, the cutting member being brought into preliminary position by this action, and an independent movement of the cutting member after the crushing action.

The instrument is simple in construction, convenient to operate, and free from objectionable corners and crevices which might prevent proper sterilization. The slender dimensions of the base and the coöperating parts afford such an instrument that will be comparatively comfortable to the patient, and which will permit of the physician or surgeon operating in a much more efficient manner than heretofore possible.

I have illustrated a preferred and satisfactory embodiment of my invention, but it is obvious that changes may be made therein within the spirit and scope thereof, as defined in the appended claims.

I claim:

1. A surgical instrument of the character described, comprising a support, a cutting member carried by said support, a secondary coöperating member carried by said support, means for reciprocating said coöperating secondary member, and means independent of said secondary member for reciprocating said cutting member.

2. A surgical instrument of the character described, comprising a support and a handle therefor, a cutting member carried by said support, a secondary coöperating member carried by said support, means for reciprocating said secondary coöperating member, means for reciprocating said cutting member, and members coöperatively connecting said means whereby reciprocation of said secondary member reciprocates said cutting member through a portion of its full movement, said means for reciprocating said cutting member having free reciprocating movement relatively to said secondary member and adapted to effect full movement of said cutting member.

3. A surgical instrument of the character described, comprising a support and a handle therefor, a cutting member carried by said support, a secondary coöperating member carried by said support, means for reciprocating said secondary member, and a rigid extension on said cutting member, adapted to be engaged by the thumb of the hand engaging said handle to independently reciprocate said cutting member.

4. A surgical instrument of the character described, comprising a support and a handle therefor, a cutting member carried by said support, a secondary coöperating member carried by said support, said cutting member having free sliding movement to slide relatively to said secondary coöperating member, means for reciprocating said cutting member, and means for reciprocating said secondary coöperating member.

5. A surgical instrument of the character described, comprising a support and a handle therefor, a cutting member carried by said support and slidable longitudinally thereof, a gripping and crushing member carried by said support and slidable longitudinally thereof, means coöperatively connecting said cutting member and said gripping and crushing member and adapted to reciprocate said cutting member as said gripping and crushing member is reciprocated, said cutting member being normally free to slide relatively to said gripping and crushing member, and means for effecting the free sliding movement of said cutting member.

6. A surgical instrument of the character described, comprising a support and a handle therefor, a cutting member carried by said support, a secondary coöperating member carried by said support, said members having a pin and slot connection whereby reciprocation of said secondary member reciprocates said cutting member, said slot permitting a further free movement of said cutting member independent of said secondary member, means for effecting the reciprocation of said secondary member, and means independent of said secondary member for effecting independent movement of said cutting member.

7. A surgical instrument of the character described, comprising a support and a handle therefor, a cutting member carried by said support, a secondary coöperating member carried by said support, said cutting member being normally free to slide relatively to said secondary coöperating member, means on said secondary member adapted to be engaged by the thumb of the hand engaging said handle for reciprocating the same, and means on said cutting member independent of said secondary member adapted to be engaged by the thumb of the hand engaging said handle to effect independent movement of said cutting member.

8. A surgical instrument of the character described, comprising a support, an apertured head at one end of said support, a cutting member carried by said support, a secondary coöperating member carried by said support, means for independently reciprocating said cutting member and said secondary member with respect to said apertured head, and an abutment in the path of said secondary member adapted to form therewith a gripping and crushing means.

9. A surgical instrument of the character described, comprising a support, an apertured head at one end of said support, a cutting member carried by said support, a secondary coöperating member carried by said support, means for independently reciprocating said cutting member and said secondary member with respect to said apertured head, and an abutment in the path of said secondary member adapted to form therewith a gripping and crushing means, and means engaging said secondary member and adapted to prevent rearward movement thereof.

10. A surgical instrument of the character described, comprising a support, a head at one end of said support, a cutting member carried by said support, a secondary member carried by said support, means for independently reciprocating said cutting member and said secondary member with respect to said head, said head having an aperture normally forwardly of the forward ends of said cutting member and said secondary member, said members adapted to be reciprocated across said aperture, and an abutment in the path of said secondary member adapted to form therewith a gripping and crushing means, and means engaging said secondary member and adapted to prevent rearward movement thereof.

11. A surgical instrument of the character described, comprising a support, a cutting member carried by said support and comprising a slide, and a cutting blade interlockingly engaged with said slide and adapted to be disengaged by being lifted therefrom, and a removable secondary coöperating member slidably disposed upon said cutting member extending over the interlocking portions of said slide and cutting blade, and adapted to maintain said interlocking engagement, and means for reciprocating said cutting member and said secondary member.

12. A surgical instrument of the character described, comprising a support, an apertured head at one end of said support, guide flanges at the sides of said head provided with two pairs of guide grooves, one of said pairs being wider than the other, a cutting member slidably mounted in one of said pairs of grooves, and a secondary member slidably mounted in said other pair of grooves, said difference in width of said pairs of grooves adapted to prevent interchangeability of said cutting member and said secondary member.

13. A surgical instrument of the character described, comprising a support provided with opposed guide flanges having inclined upwardly converging inner surfaces, a cutting member carried by said support, a secondary coöperating member carried by said support and disposed above said cutting member, a portion of the opposed edges of said secondary member being inclined to interlockingly and slidably engage said inner surfaces of said guide flanges to retain said cutting member and said secondary member upon said support, another portion of said secondary member being reduced relatively to said flanges to permit disengagement of said secondary member from said support.

14. A surgical instrument of the character described, comprising a support having an eye, a cutting member carried by said support and having an elongated slot to register with said eye, a secondary coöperating member carried by said support and having an elongated slot to register with said eye and provided with ratchet teeth, a connection means comprising a stem adapted to engage said eye of said support and said slots of said members, and having a head at one end adapted to be turned crosswise relatively to said eye, and a spring retention member at the other end of said stem adapted to engage the upper side of said secondary member and having a tooth adapted to engage said ratchet teeth to prevent rearward movement of said secondary member, and means for reciprocating said cutting member and said secondary member.

15. A surgical instrument of the character described, comprising a support having an eye, a cutting member carried by said support having an elongated slot to register with said eye, a secondary coöperating member carried by said support and having an elongated slot to register with said eye, and provided with a longitudinal groove and with ratchet teeth, and connection means comprising a stem adapted to engage said eye of said support and said slots of said members and having a head at one end adapted to be turned crosswise relatively to said eye, and a spring retention member at the other end of said stem adapted to be engaged at the upper side of said secondary member having a pin slidably engaging said slot of said secondary member and having teeth adapted to engage said ratchet teeth to prevent rearward movement of said secondary member, and means for reciprocating said cutting member and said secondary member.

16. A surgical instrument of the character described, comprising a support, a cutting member carried by said support, a secondary coöperating member carried by said support, and means for independently reciprocating said cutting member and said secondary coöperating member, said means for reciprocating said secondary member comprising a rotary cam wedge, and means cooperating therewith adapted to reciprocate said secondary member with relatively great force.

17. A surgical instrument of the character described, comprising a support, a cutting member carried by said support, a secondary coöperating member carried by said support, and means for independently reciprocating said cutting member and said secondary coöperating member, said means for reciprocating said secondary member comprising a rotary cam wedge carried by said secondary member, means for limiting the movement thereof, and means carried by said support coöperating therewith, and adapted to reciprocate said secondary member with relatively great force.

18. A surgical instrument of the character described, comprising a support, a cutting member carried by said support, a secondary coöperating member carried by said support, and means for independently reciprocating said cutting member and said secondary coöperating member, said means for reciprocating said secondary member comprising a rotary cam wedge, means for frictionally retaining said cam wedge in any position of movement, and means coöperating therewith adapted to reciprocate said secondary member with relatively great force.

19. A surgical instrument comprising a support, a sliding member carried by said support, means for sliding said member upon the support to effective position including an adjustable element comprising a rotary beveled cam carried by and movable with said sliding member in the sliding movement thereof, and a fixed part with which said element is adapted to coact, the rotation of the cam riding the bevel of the cam on the fixed part.

20. A surgical instrument comprising a support, a sliding member carried by said support, and means for reciprocating said member including an adjustable element connected to said member, said adjustable member having a rotary beveled cam and means preventing relative longitudinal movement of said reciprocating member and adjustable element, and a relatively fixed part with which said element is adapted to coact, the rotation of the cam riding the bevel of the cam on the fixed part.

21. A surgical instrument comprising a support, a sliding member carried by said support, means for initially shifting the sliding member on the support to its effective position, and additional means for subsequently imparting a further sliding movement to said member including an adjustable element having a rotary beveled cam carried by and movable with said member in the latter sliding movement thereof, and a fixed part with which said element is adapted to coact, the rotation of the cam riding the bevel of the cam on the fixed part.

22. A surgical instrument comprising a support, a sliding member carried by said support, and means for reciprocating said member including a rotary cam element beveled at one side carried by said member and secured against longitudinal movement relative thereto, and a relatively fixed part with which said rotary cam element is adapted to coact, the rotation of the cam riding the bevel of the cam on the fixed part.

23. A surgical instrument comprising a support, a sliding member carried by said support, means for initially shifting the sliding member on the support to its effective position, and cam means beveled at one side carried by and movable with said member in such initial movement thereof, said cam means adapted to coact with a fixed part on the support to impart a further sliding movement to said member, the rotation of the cam riding the bevel of the cam on the fixed part.

GEORGE ERMOLD.